(12) United States Patent (10) Patent No.: US 12,622,709 B1

Henderson (45) Date of Patent: May 12, 2026

(54) TRAJECTORY AND AIMING GUIDE FOR USE WITH FLUOROSCOPY

(71) Applicant: Dartmouth-Hitchcock Clinic, Lebanon, NH (US)

(72) Inventor: Eric R. Henderson, Lebanon, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 149 days.

(21) Appl. No.: 18/513,634

(22) Filed: Nov. 20, 2023

Related U.S. Application Data

(63) Continuation of application No. 16/532,298, filed on Aug. 5, 2019, now Pat. No. 11,819,225, which is a continuation of application No. 15/015,089, filed on Feb. 3, 2016, now Pat. No. 10,390,843.

(60) Provisional application No. 62/111,636, filed on Feb. 3, 2015.

(51) Int. Cl.
*A61B 17/17* (2006.01)
*A61B 6/58* (2024.01)

(52) U.S. Cl.
CPC .......... *A61B 17/1703* (2013.01); *A61B 6/587* (2013.01)

(58) Field of Classification Search
CPC ...... A61B 17/17–1721; A61B 17/1796; A61B 17/90
USPC ....................................... 606/97; 378/204, 42
See application file for complete search history.

(56) References Cited

U.S. PATENT DOCUMENTS

| | | | |
|---|---|---|---|
| 1,370,640 | A | 3/1921 | Granger |
| 2,666,430 | A | 1/1954 | Gispert |
| 4,803,976 | A | 2/1989 | Frigg |
| 5,013,317 | A | 5/1991 | Cole |
| 5,026,239 | A | 6/1991 | Chiba |
| 5,030,222 | A | 7/1991 | Calandruccio |
| 5,031,203 | A | 7/1991 | Trecha |
| 5,212,720 | A | 5/1993 | Landi |
| 5,283,808 | A | 2/1994 | Cramer |
| 5,285,785 | A | 2/1994 | Meyer |
| 5,426,687 | A | 6/1995 | Goodall |
| 6,475,168 | B1 | 11/2002 | Pugsley |
| 6,527,443 | B1 | 3/2003 | Vilsmeier |
| 7,083,624 | B2 | 8/2006 | Irving |
| 7,207,714 | B1 | 4/2007 | Dhillon |
| 7,674,264 | B2 | 3/2010 | Feiler |
| 8,382,758 | B1 | 2/2013 | Sommers |
| 2002/0058948 | A1 | 5/2002 | Arlettaz |
| 2003/0130576 | A1* | 7/2003 | Seeley ................... A61B 90/36 600/426 |

(Continued)

*Primary Examiner* — Amy R Sipp

(74) *Attorney, Agent, or Firm* — Loginov & Associates, PLLC; William A. Loginov

(57) ABSTRACT

A system for a trajectory and aiming guide for use with fluoroscopy is comprised of a ring holder is with a plurality of connecting arms, a radiolucent ring disk with an outer perimeter wall and a central axle on the bottom surface of the ring disk; a first rotatable disk located below the ring holder and comprised of a handle, a radiolucent disk ring with a central cutout to receive the central axle, the material of the disk comprising an embedded array of a plurality of radiopaque wires and an outer perimeter wall; a second rotatable disk located below the first rotatable disk and comprised of a handle, a radiolucent disk ring with a central cutout to receive the central axle, the material of the disk comprising an embedded array of a plurality of radiopaque wires and an outer perimeter wall; and a locking cap for the axle.

13 Claims, 6 Drawing Sheets

(56)                    References Cited

U.S. PATENT DOCUMENTS

| | | |
|---|---|---|
| 2004/0138667 A1 | 7/2004 | Kimura |
| 2006/0235420 A1 | 10/2006 | Irving |
| 2010/0312103 A1 | 12/2010 | Gorek |
| 2013/0178863 A1* | 7/2013 | Kubiak ................. A61B 6/485 |
| | | 606/102 |
| 2014/0163557 A1 | 6/2014 | Beyar |
| 2014/0163563 A1 | 6/2014 | Reynolds |
| 2014/0163570 A1 | 6/2014 | Reynolds |
| 2015/0257846 A1 | 9/2015 | Kubiak |

* cited by examiner

TRAJECTORY AND AIMING GUIDE FOR USE WITH FLUOROSCOPY

RELATED APPLICATIONS

This application is a continuation of co-pending U.S. patent application Ser. No. 16/532,298, entitled TRAJECTORY AND AIMING GUIDE FOR USE WITH FLUOROSCOPY, filed Aug. 5, 2019, which is a continuation of co-pending U.S. patent application Ser. No. 15/015,089, entitled TRAJECTORY AND AIMING GUIDE FOR USE WITH FLUOROSCOPY, filed Feb. 3, 2016, now U.S. Pat. No. 10,390,843, issued Aug. 27, 2019, which claims the benefit of U.S. Provisional Application Ser. No. 62/111,636, entitled TRAJECTORY AND AIMING GUIDE FOR USE WITH FLUOROSCOPY, filed Feb. 3, 2015, the entire disclosure of each of which applications is herein incorporated by reference.

FIELD OF THE INVENTION

This invention is in the field of medical devices, and more particularly devices for aiming objects inserted into the body using x-rays.

BACKGROUND OF THE INVENTION

Fluoroscopy is used for determining the alignment and placement of invasive medical implants (for example, surgical screws) that are inserted into a body. Fluoroscopes using x-ray emissions are a significant tool in orthopaedic procedures. Proper alignment and placement of implants reduces adverse outcomes and complications for the patient. The ultimate goal of the surgeon is to repair or replace a non-functional joint with a joint that functions as naturally as possible. Poor placement can result in harm to adjacent organs or tissues (for example, nerves and blood vessels), discomfort, gait problems, degradation of the prostheses and possible revision surgery.

Fluoroscopic checks during surgery give the surgeon an opportunity to properly align and place the implants. This is of particular importance for the proper trajectory of screws. A surgeon who is able to quickly make a correct determination of alignment and seating of the implants leads to a shorter surgical time, which can result in a reduced tourniquet time, reduced anesthesia time, lower blood loss, and improved recovery by the patient. Implant penetration depth can be ascertained. Furthermore, frequent fluoroscopic checks increases the amount of ambient ionized radiation in the operating room, which can pose a long-term health risk for the patient and surgical team. Improvements in vision technology and shielded garments can reduce the amount of radiation, but not all of the risks of exposure.

It would be desirable to have an alignment system for properly aligning the surgical implants as quickly as possible, resulting in a better outcome for the patient and less exposure to radiation for the surgical team.

SUMMARY OF THE INVENTION

The present invention overcomes the disadvantages of the prior art by providing a system and method for a trajectory and aiming guide for use with fluoroscopy. The trajectory and aiming guide is comprised of a ring holder with a plurality of connecting arms, a radiolucent ring disk with an outer perimeter wall and a central axle on the bottom surface of the ring disk; a first rotatable disk located below the ring holder and comprised of a handle, a radiolucent disk ring with a central cutout to receive the central axle, the material of the disk comprising an embedded array of a plurality of radiopaque wires and an outer perimeter wall; a second rotatable disk located below the first rotatable disk and comprised of a handle, a radiolucent disk ring with a central cutout to receive the central axle, the material of the disk comprising an embedded array of a plurality of radiopaque wires and an outer perimeter wall; and a locking cap for the axle. The trajectory and aiming guide is removably attachable to an x-ray receiver of a fluoroscope. The embedded array of a plurality of wires in a rotatable disk can be arranged in a parallel orientation. The embedded array of a plurality of wires in a rotatable disk can be arranged equidistant from one another. The embedded array of a plurality of wires in a rotatable disk can be arranged in a converging orientation. The ring holder can define four connecting arms. The outer perimeter walls of at least one rotatable disk define indicia markings. The first rotatable disk and the second rotatable disk can be interchangeable with each other. The rotatable disk having embedded wires in a parallel array can be interchanged with a rotatable disk having embedded wires in a converging array. A method for determining the angular trajectory and alignment of objects inserted using x-rays using a trajectory and aiming guide is comprised of the steps of attaching the trajectory and aiming guide to a x-ray receiver of a fluoroscope; rotating a first rotatable disk to align embedded wire lines with a first reference axis; rotating a second rotatable disk to align embedded wire lines with a second reference axis; determining the angular difference between the alignment of the first rotatable disk and the alignment of the second rotatable disk.

BRIEF DESCRIPTION OF THE DRAWINGS

The invention description below refers to the accompanying drawings, of which.

DETAILED DESCRIPTION

Figures 1, 2:
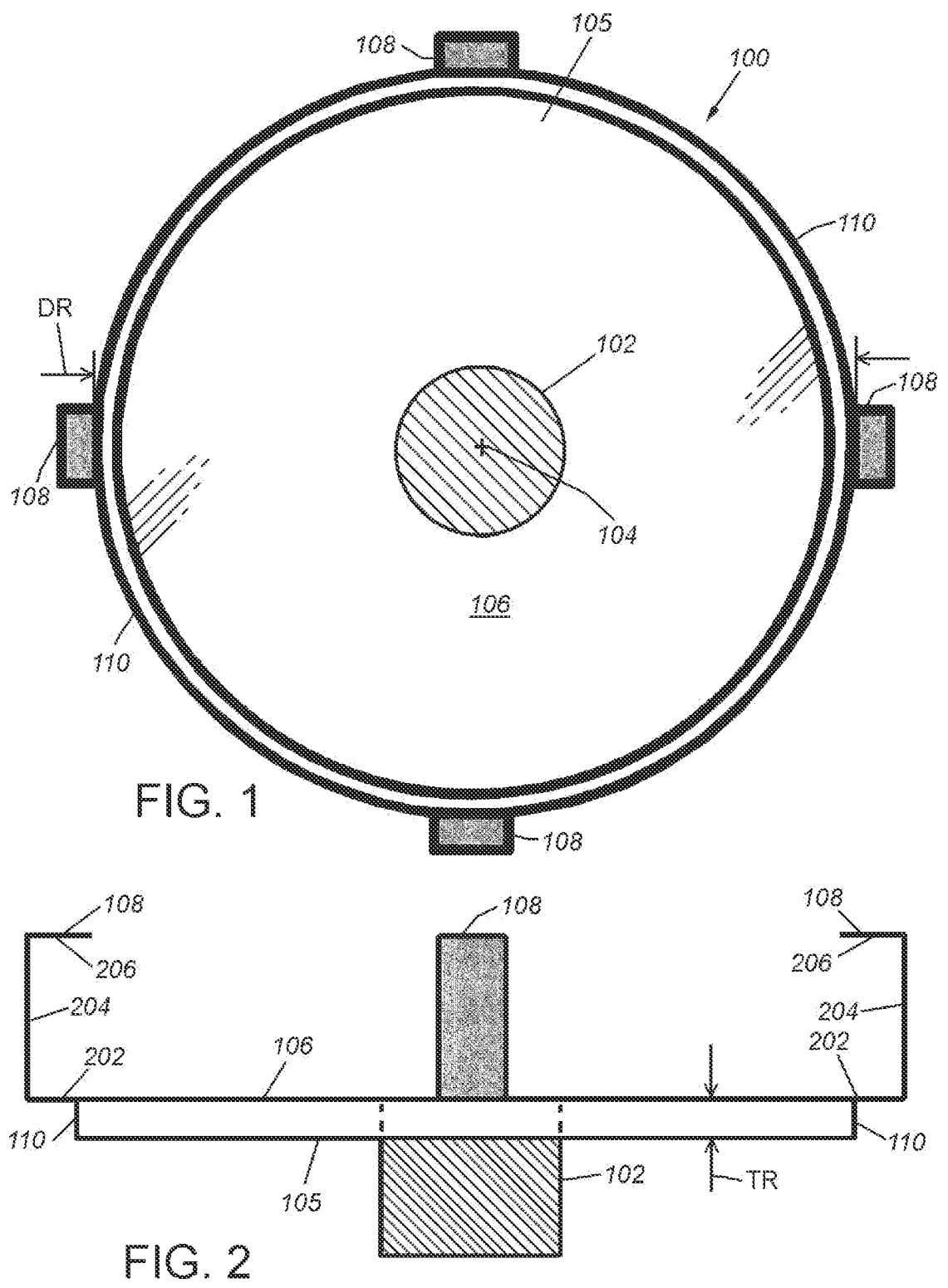
FIG. 1 is a bottom view of a ring holder for a trajectory and aiming guide according to an illustrative embodiment.
FIG. 2 is a side view of a ring holder for a trajectory and aiming guide according to the illustrative embodiment.

In an embodiment, a trajectory and aiming guide includes three parallel round disks, two of which are mounted and rotate around a central vertical axle. The disk diameters are dimensioned so as to approximate the diameter of the x-ray receiver of the fluoroscopy machine. FIG. 1 depicts an exemplary ring holder 100. A central axle 102 is mounted and aligned on the center 104 of bottom surface 105 of the ring 100. The central axle 102 is aligned with the stream of x-rays, in an up and down orientation with regards to the x-ray receiver. The ring disk 106 describes a solid x-ray translucent ("radiolucent") disk that mounts over the x-ray receiver of the fluoroscopy machine using four mounting clips 108 disposed around the outer perimeter 110 of the ring disk 106. The ring disk 106 is therefore a mounting element that fixes the device to a fluoroscope with a stable connection. The mounting clips 108 describe connecting arms for that stable connection. In alternate embodiments, the mounting clips 108 can be constructed as mounting clamps with spring-loaded tension mechanisms, snaps, or another clamping lock. In other embodiments, it is contemplated that there can be more or fewer mounting clips. The ring holder 100 receives and retains the two rotatable rings 300, 500. The material of the ring is a rigid x-ray translucent material, for example, high-density polyethylene (HDPE) or any radiolucent material with adequate rigidity to support the radiopaque wires. The outer diameter DR of the ring holder is approximately 16 inches (406 mm). As noted, the outer diameter DR can vary greater or lesser depending on the diameter of the x-ray receiver of the fluoroscopy machine. In an embodiment, a fluoroscopy receiver is provided with a diameter of 15.25 inches (387 mm).

FIG. 2 is a side view of the ring holder 100 of FIG. 1. The thickness TR of the ring 106 is approximately one-quarter inch (6 mm). In other embodiments, this thickness can vary greater or lesser. The clips 108 are "U-shaped" and have a base 202, vertical portion 204 and overhang 206 and are constructed to removably attach to the fluoroscope x-ray receiver (not shown).

Figure 3:
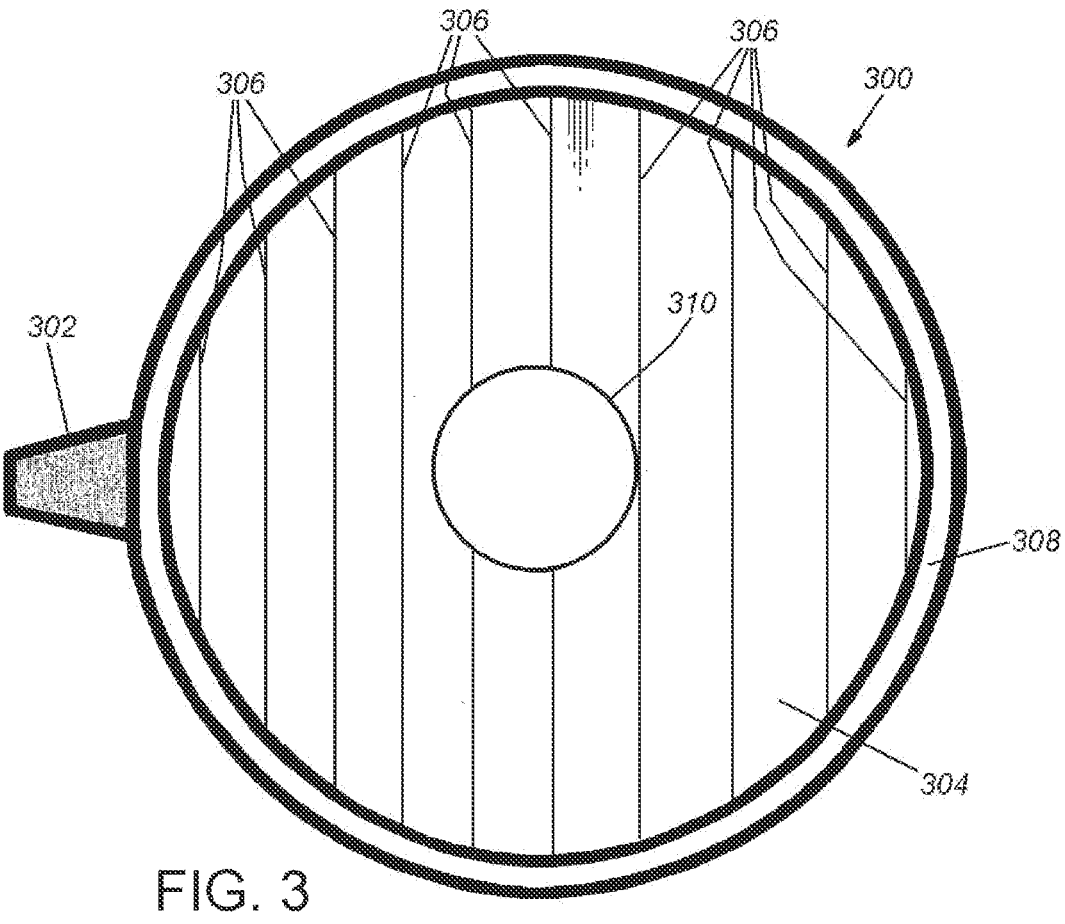
FIG. 3 is a bottom view of an upper ring for a trajectory and aiming guide according to the illustrative embodiment.

Rotatable rings 300 and 500 have a diameter that is the same or less than the ring holder 100. In one example, the first ring disk has a diameter of sixteen inches while the rotatable discs are each 15.25 inches in diameter. An exemplary first ring disk 300 is shown in FIG. 3. This is an upper ring 300 and includes a handle 302 and a ring disk 304. The ring disk 304 is constructed of a rigid x-ray translucent material, for example, high-density polyethylene (HDPE). An array of a plurality of metal wires 306 are imbedded within the material of the ring disk 304 that are visible when seen on an x-ray machine (radiopaque). In an embodiment, ten wires are depicted as embedded within the material of the ring disk 304. In other embodiments, the number of wires can be greater or lesser, and have a regular or irregular spacing. The metal wires 306 are arranged so as to be equidistant from each other and parallel to each other. Under fluoroscopy, the disk will appear to be translucent while the wires will be visible as an array of parallel lines. The rotatable upper ring 300 rotates around axle 102 independent of the ring holder 100 and the lower ring 500 and is manipulated by the handle 302. Center cutout 310 receives the axle 102.

Figure 4:
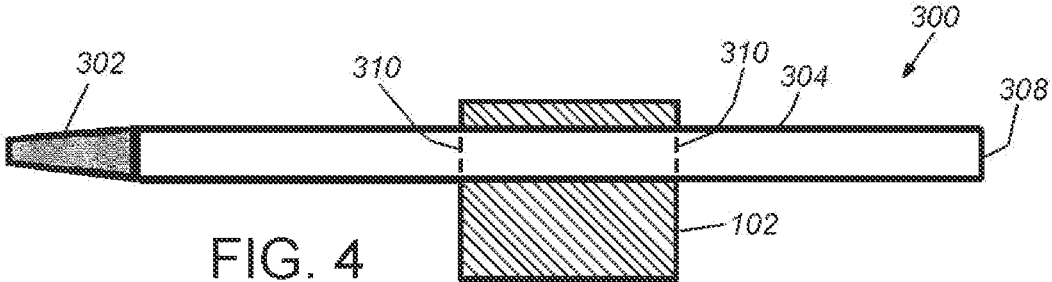
FIG. 4 is a side view of the upper ring for a trajectory and aiming guide according to the illustrative embodiment.

FIG. 4 is a side view of the upper ring 300 and central axle 102. The outer perimeter wall 308 can be provided with indicia lines and reference numbers in another embodiment.

Figure 5:
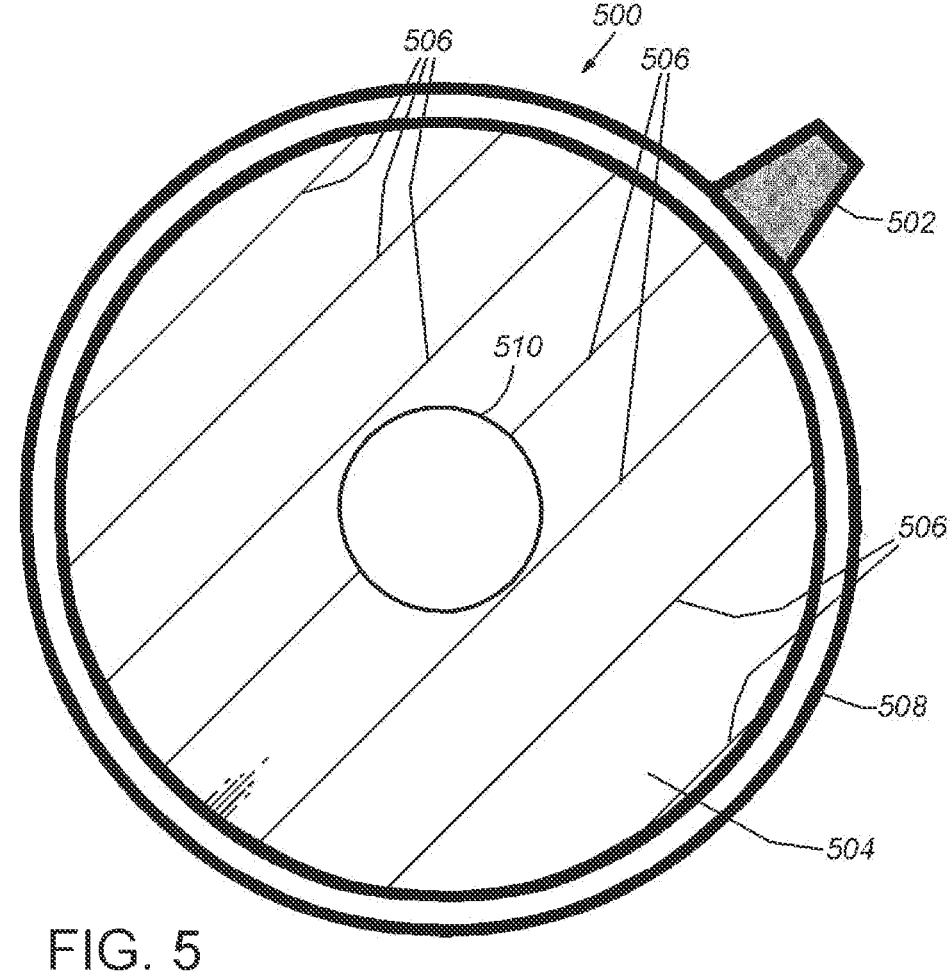
FIG. 5 is a bottom view of a lower ring for a trajectory and aiming guide according to the illustrative embodiment.

An exemplary second disk ring 500 is shown in FIG. 5. This ring is the lower ring 500 and includes a handle 502 and a ring disk 504. The ring disk 504 is constructed of the same radiolucent material as the upper disk 300. An array of a plurality of radiopaque metal wires 506 are imbedded within the material of the ring disk 504. In an embodiment, ten wires are depicted as embedded within the material of the ring disk 504. In other embodiments, the number of wires can be greater or lesser, and have a regular or irregular spacing. In an embodiment, the metal wires 506 are arranged so as to be equidistant from each other and parallel to each other. The rotatable lower ring 500 rotates around axle 102 independent of the ring holder 100 and the upper ring 300 and is manipulated by the handle 502. Center cutout 510 receives the axle 102.

Figure 6:
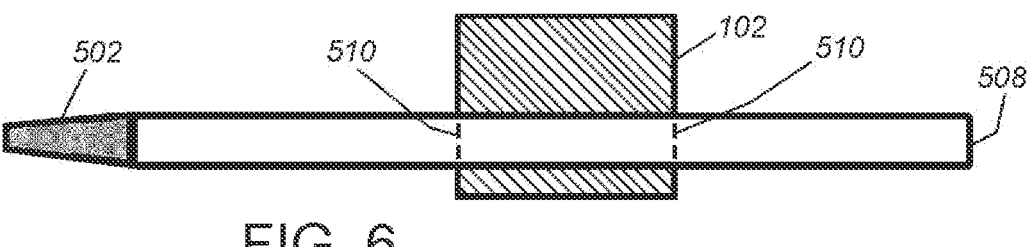
FIG. 6 is a side view of a lower ring for a trajectory and aiming guide according to the illustrative embodiment.

FIG. 6 is a side view of the lower ring 500 and central axle 102. The outer perimeter wall 508 can be provided with indicia lines and reference numbers in another embodiment.

Figure 7:
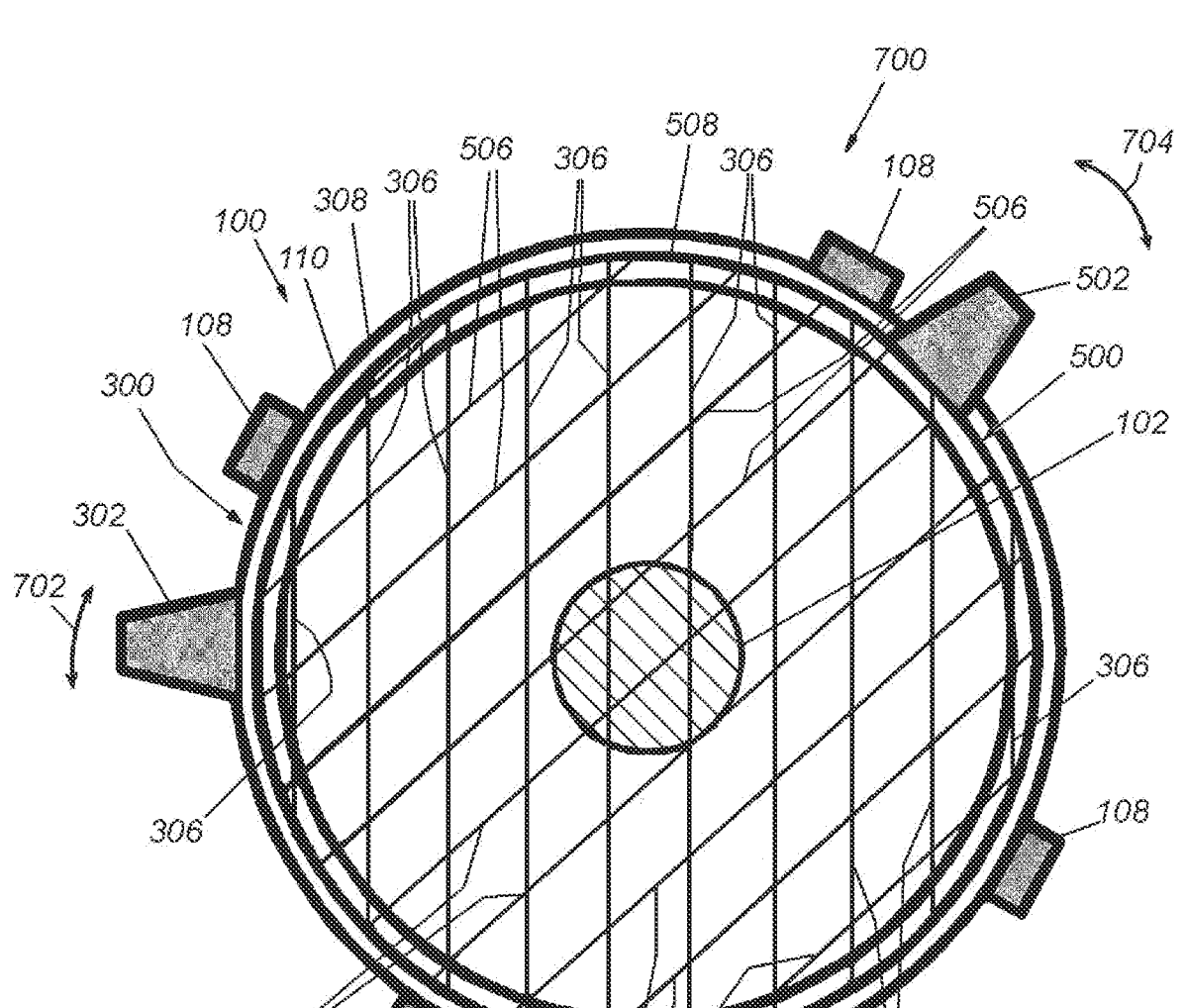
FIG. 7 is a bottom view of the combined elements of a trajectory and aiming guide according to the illustrative embodiment.

FIG. 7 is a combined view 700 of ring holder 100, upper ring disk 300 and lower ring disk 500. The imbedded wires 306, 506 are depicted relative to each other. As noted above, upper ring 300 is rotatable in a circular movement 702 around the axle 102 by manipulation of handle 302. Lower ring 500 is rotatable in a circular movement 704 around the axle 102 by manipulation of handle 502. Rotation of each ring will change the orientation of the embedded arrays of wires 306, 506. The wires 306, 506 can be oriented in parallel or converging patterns. As depicted in FIGS. 3, 5 and 7, the two rotatable disks define parallel line arrays. It is expressly contemplated that a plurality of disc configurations may be considered It is further contemplated that digitally superimposed trajectory guides can be projected in the software of the fluoroscope such that the operator can select the guide to be superimposed and change it during the operation as needed.

In use, the trajectory and aiming guide is attached to the x-ray receiver of the fluoroscope. Under the fluoroscope, the lines formed by the wires are visible, as well as the underlying bones and any implanted materials (e.g., surgical screws, plates). The angular orientations are determined by rotating the first (upper) ring to align with a first reference axis (for example, the axis of the shaft of a femur). The surgeon then rotates the second (lower) ring to align with a second reference axis (for example, the trajectory of a surgical screw). The angular difference between these two reference axes can be determined by first measuring the angles of each and subtracting the lesser angle from the higher. Indicia on the outer perimeter walls 308, 508 can be provided for reference measurement of the relative angles and to assist the calculation of the angular differences. For example, when the embedded wires 308 of the upper disk 300 are perpendicular to the wires 508 or the lower disk 500, the angular orientation is ninety (90) degrees.

For many orthopaedic applications (e.g., the implantation of percutaneous screws for a hip fracture), one of the rotatable disks can be oriented so that the embedded wires are parallel to a first reference axis, in an embodiment, the axis of the bone (e.g., the femoral shaft), and the second disk can be rotated to an orientation with a second reference axis, for example, the optimal trajectory for screw placement. The optimal trajectory can then be used for implanting the screw. Given that the angular orientation of joints and bones can vary from patient to patient, the precise measurement and calculation of these angular orientations can result in a more efficacious outcome and recovery for the patient.

Once the surgeon has rotated the disks to establish the optimal angular orientation, the disks can be left in position and the lines of the wires used to chart the optimal entry position for the first and subsequent screws. This avoids the surgeon having to make additional holes and the resultant weakening of the bone that result from multiple holes. Furthermore, the surgeon can record the alignments and setting for future reference, both for medical records and for possible future surgeries.

Figure 8:
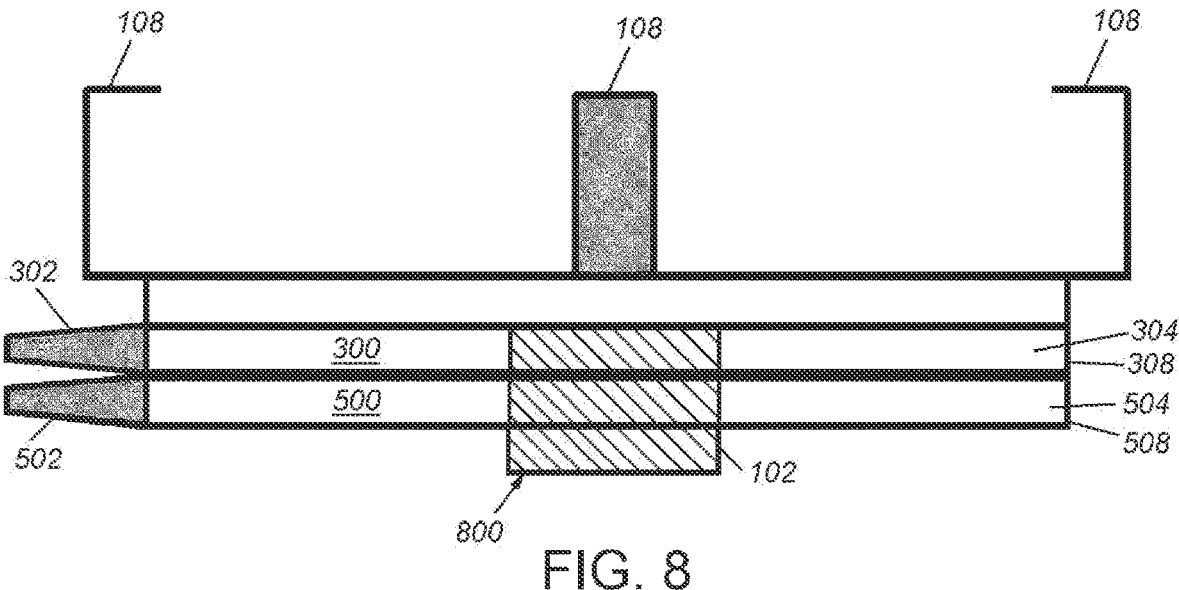
FIG. 8 is a side view of the trajectory and aiming guide according to the illustrative embodiment.

FIG. 8 is a side view of the elements of FIG. 7. The rotatable disks 300, 500 can be secured to the axle 102 by an axle locking mechanism, in this embodiment, an exemplary locking end cap 800. In other embodiments, the axle locking mechanism 800 can be a threaded ring, threaded cap, spring-loaded lock or another such mechanism.

Figure 9:
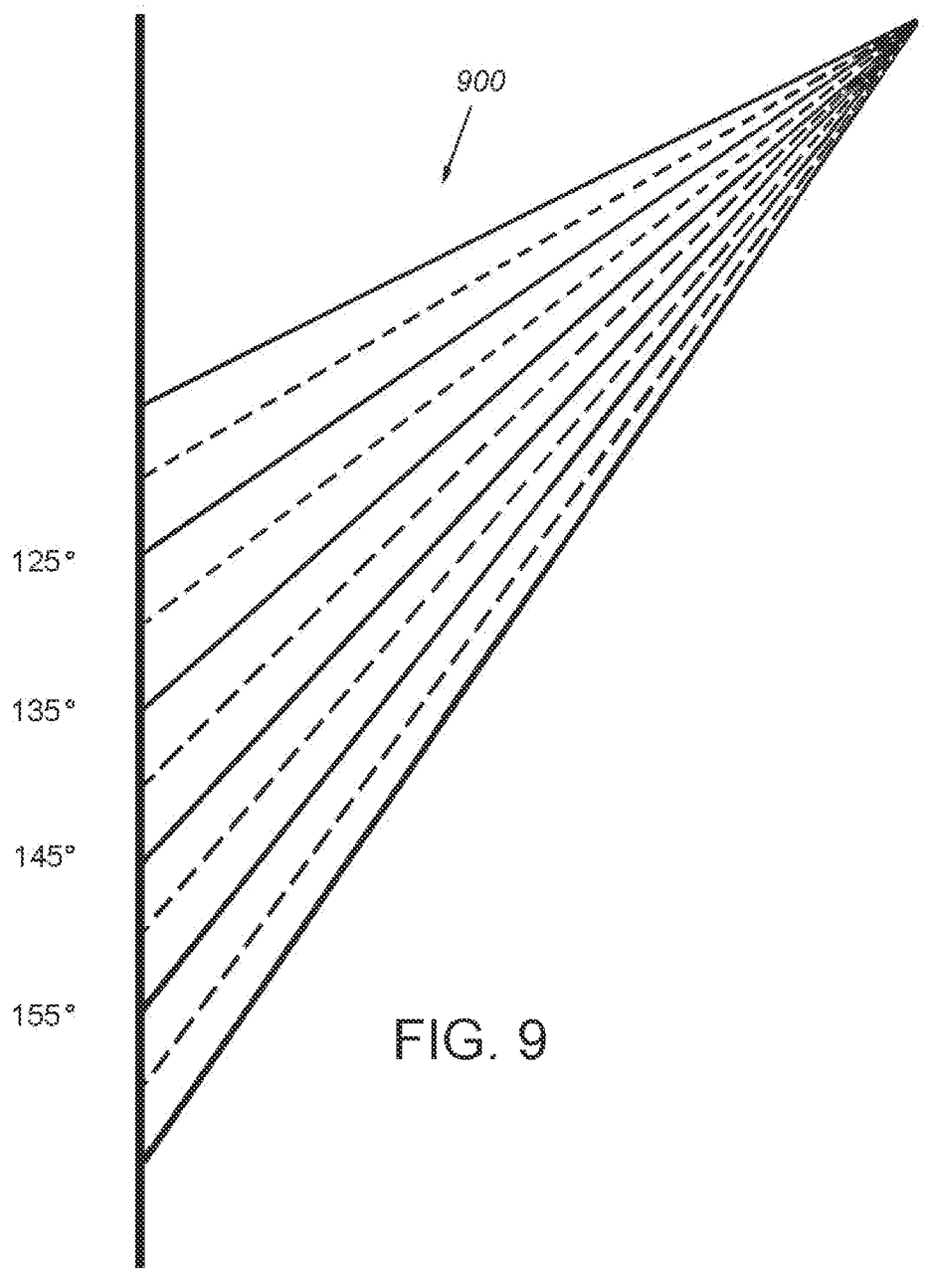
FIG. 9 is a schematic view of a hip screw center-center aiming guide according to an alternate embodiment.

FIG. 9 is an alternate embodiment showing a different alignment scheme 900 for the imbedded wires 306, 506, to create a converging pattern of implanted devices. This alignment guide can be used in the event a dynamic hip screw implant was combined with an anti-rotation screw. Given that the axle locking mechanism 800 can be removed, it is expressly contemplated that one of or both of the rotatable rings 300, 500 can be substituted with a disk provided with the different alignment scheme 900. As used herein the directional terms, such as, but not limited to, "up" and "down", "upward" and "downward", "rear", "rearward" and "forward", "top" and "bottom", "inside" and "outer", "front" and "back", "inner" and "outer", "interior" and "exterior", "downward" and "upward", "horizontal" and "vertical" should be taken as relative conventions only, rather than absolute indications of orientation or direction with respect to a direction of the force of gravity.

It should be clear from the foregoing that the above-described device provides for an accurate and readily used system for the determination of angular orientations of bones and implantable devices by fluoroscopy. Such determinations are useful to a broad range of surgical procedures, from repairs to replacements. This can improve hip and shoulder replacements, spinal surgeries and a wide range of other procedures.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, a locking mechanism can be provided that locks each disk when the proper orientation for that disk is established. The outer perimeter wall can be provided with a sensor that determines the angular orientation with regard to a reference point for that disk for display on the fluoroscope or a secondary display. As noted, the disks can be provided with embedded wire arrays that are in parallel or converging orientations. There can be more or fewer embedded wires. The disks can be interchangeable. In other embodiments, the disks can be provided with a small servo motor and a power source and rotated by a remote control. Accordingly, this description is meant to be taken only by way of example, and not to otherwise limit the scope of this invention.

What is claimed is:

1. A method for determining angular trajectory and alignment of objects inserted using x-rays using a trajectory and aiming guide, the method comprising:

attaching a trajectory and aiming guide over an x-ray receiver of a fluoroscope;

rotating a first rotatable disk of the trajectory and aiming guide comprising radiopaque wire lines to define a first reference axis, the first rotatable disk including indicia for measurement of relative angles;

defining a second reference axis with a second rotatable disk of the trajectory and aiming guide that rotates independently of the first rotatable disk; and determining an angular difference between an alignment of one of the radiopaque wire lines of the first rotated rotatable disk and the second reference axis, the angular difference being based on a relationship of the second reference axis with the indicia for measurement of relative angles of the rotated first rotatable disk.

2. The method of claim 1, wherein the indicia are disposed on a perimeter wall of the first rotatable disk.

3. The method of claim 1, wherein rotating the first rotatable disk includes rotating the first rotatable disk relative to the x-ray receiver.

4. The method of claim 1, wherein the first rotatable disk is rotatably attached to a portion of the trajectory and aiming guide that is fixed relative to the x-ray receiver.

5. The method of claim 1, wherein the first reference axis includes an orientation of a target fluoroscopy subject.

6. The method of claim 1, wherein the second reference axis includes a target trajectory for screw placement.

7. The method of claim 1, wherein the radiopaque wire lines of the first rotatable disk are substantially parallel.

8. The method of claim 1, wherein the radiopaque wire lines of the first rotatable disk converge.

9. The method of claim 1, wherein the radiopaque wire lines facilitate determining target entry position for a surgical screw.

10. A method for determining a target trajectory of surgical objects, the method comprising steps of:

attaching a trajectory and aiming guide over an x-ray receiver of a fluoroscope;

aligning radiopaque wire lines of a first rotatable disk of the attached trajectory and aiming guide with a first reference axis;

identifying a position of indicia for measurement of relative angles, wherein the indicia are disposed on an outer perimeter of the first rotatable disk;

aligning radiopaque wire lines of a second independently rotatable disk of the attached trajectory and aiming guide with a second reference axis based on a bone of a surgical subject; and determining a target trajectory and a point of entry of at least one surgical object based on a relationship of the first reference axis to the second reference axis and the position of the indicia for measurement of relative angles.

11. The method of claim 10, wherein the radiopaque wire lines of the first rotatable disk are substantially parallel.

12. The method of claim 10, wherein the radiopaque wire lines of the first rotatable disk converge.

13. The method of claim 10, wherein the target trajectory defines a target orientation and alignment for a medical device or implant.

* * * * *